(12) United States Patent
Guo

(10) Patent No.: US 12,706,218 B2
(45) Date of Patent: Aug. 11, 2026

(54) BLOOD PARAMETER ASSESSMENT SYSTEMS AND METHODS

(71) Applicant: SHANGHAI UNITED IMAGING HEALTHCARE CO., LTD., Shanghai (CN)

(72) Inventor: Jian Guo, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 1005 days.

(21) Appl. No.: 17/822,762

(22) Filed: Aug. 26, 2022

(65) Prior Publication Data

US 2023/0060613 A1 Mar. 2, 2023

(30) Foreign Application Priority Data

Aug. 26, 2021 (CN) ........................ 202110987269.3
Aug. 26, 2021 (CN) ........................ 202110987973.9

(51) Int. Cl.
*G16H 50/50* (2018.01)
*A61B 5/02* (2006.01)

(52) U.S. Cl.
CPC ............... *G16H 50/50* (2018.01); *A61B 5/02* (2013.01); *G06T 2207/30104* (2013.01)

(58) Field of Classification Search
CPC ........ G16H 50/50; G16H 30/40; G16H 50/20; G16H 50/70; A61B 5/02; A61B 2034/102;

(Continued)

(56) References Cited

U.S. PATENT DOCUMENTS

2012/0022843 A1 1/2012 Ionasec et al.
2013/0197884 A1 8/2013 Mansi et al.

(Continued)

FOREIGN PATENT DOCUMENTS

CN 104116563 A 10/2014
CN 108294735 A 7/2018

(Continued)

OTHER PUBLICATIONS

Razavi SE, Zanbouri R, Arjmandi-Tash O. Simulation of blood flow coronary artery with consecutive stenosis and coronary-coronary bypass. BioImpacts: BI. Aug. 5, 2011;1(2):99. (Year: 2011).*

(Continued)

*Primary Examiner* — Chuen-Meei Gan
(74) *Attorney, Agent, or Firm* — METIS IP LLC

(57) ABSTRACT

The present disclosure may provide blood parameter assessment systems and methods. The systems may acquire specific data of an object. The systems may determine a first model of the object. The first model may include cardiac anatomy information of at least a portion of a heart of the object. The systems may determine a first blood parameter of the object based on the specific data of the object and the first model of the object. The systems may determine a second model of the object. The second model may include a configuration of a grafted vessel of the object. The systems may determine a second blood parameter of the object based on the specific data of the object and the second model of the object. The systems may determine a quantification result of the object based on the first blood parameter and the second blood parameter.

19 Claims, 6 Drawing Sheets

(58) Field of Classification Search
CPC ........ A61B 2034/104; A61B 2034/105; A61B 34/10; G06T 2207/30104
See application file for complete search history.

(56) References Cited

U.S. PATENT DOCUMENTS

| | | | | |
|---|---|---|---|---|
| 2014/0249399 | A1 | 9/2014 | Sharma et al. | |
| 2014/0372096 | A1* | 12/2014 | Spilker | G16H 50/20 703/11 |
| 2015/0242589 | A1 | 8/2015 | Neumann et al. | |
| 2018/0032653 | A1* | 2/2018 | Aben | G06F 30/20 |

FOREIGN PATENT DOCUMENTS

| | | | |
|---|---|---|---|
| CN | 109700475 | A | 5/2019 |
| CN | 110575252 | A | 12/2019 |
| CN | 111312375 | A | 6/2020 |
| CN | 111652849 | A | 9/2020 |
| CN | 112382397 | A | 2/2021 |
| CN | 113133827 | A | 7/2021 |
| KR | 20190125596 | A | 11/2019 |

OTHER PUBLICATIONS

Jolanda J. Wentzel et al., Endothelial Shear Stress in the Evolution of Coronary Atherosclerotic Plaque and Vascular Remodelling: Current Understanding and Remaining Questions, Cardiovascular Research, 2012, 10 pages.

Foad Kabinejadian et al., In Vitro Measurements of Velocity and Wall Shear Stress in a Novel Sequential Anastomotic Graft Design Model Under Pulsatile Flow Conditions, Medical Engineering & Physics, 36: 1233-1245, 2014.

First Office Action in Chinese Application No. 202110987269.3 mailed on Jul. 1, 2022, 21 pages.

* cited by examiner

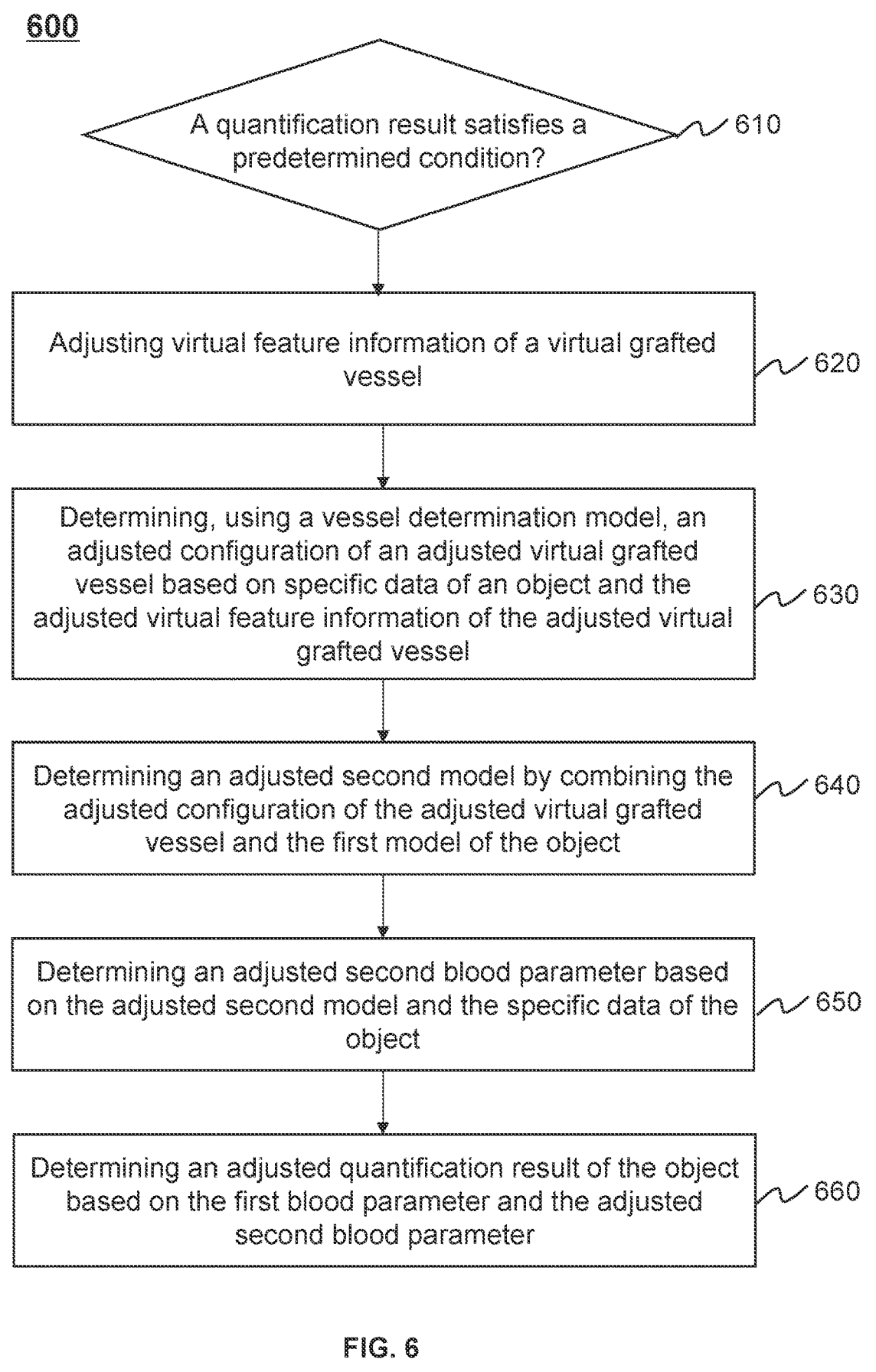

600

A quantification result satisfies a predetermined condition? 610

Adjusting virtual feature information of a virtual grafted vessel 620

Determining, using a vessel determination model, an adjusted configuration of an adjusted virtual grafted vessel based on specific data of an object and the adjusted virtual feature information of the adjusted virtual grafted vessel 630

Determining an adjusted second model by combining the adjusted configuration of the adjusted virtual grafted vessel and the first model of the object 640

Determining an adjusted second blood parameter based on the adjusted second model and the specific data of the object 650

Determining an adjusted quantification result of the object based on the first blood parameter and the adjusted second blood parameter 660

FIG. 6

BLOOD PARAMETER ASSESSMENT SYSTEMS AND METHODS

CROSS-REFERENCE TO RELATED APPLICATIONS

This application claims priority to Chinese Patent Application No. 202110987973.9, filed on Aug. 26, 2021 and Chinese Patent Application No. 202110987269.3, filed on Aug. 26, 2021, the contents of each of which are hereby incorporated by reference.

TECHNICAL FIELD

The present disclosure generally relates to a medical field, and more particularly, relates to blood parameter assessment.

BACKGROUND

Coronary artery disease (CAD) may affect an artery of a patient that supplies blood to the heart of the patient. CAD is usually caused by atherosclerosis. Atherosclerosis is a buildup of plaque inside an artery wall, causing the artery wall to become thickened and stiff, and the lumen of the artery to become narrow, which in turn may slow down a flow of blood in the lumen of the artery, resulting in one or more symptoms including, such as, myocardial ischemia, hypoxia, necrosis, etc. When a coronary artery stenosis reaches a threshold (e.g., 75%), an interventional therapy (e.g., a bypass surgery) is needed to alleviate the symptom (s). Therefore, it is desirable to provide a method and system for efficiently planning and/or assessing an interventional therapy of CAD.

SUMMARY

According to some embodiments of the present disclosure, a system may be provided. The system may include: at least one storage device including a set of instructions; at least one processor in communication with the at least one storage device, wherein when executing the set of instructions, the at least one processor may be configured to cause the system to perform operations including: acquiring specific data of an object; determining a first model of the object, the first model comprising cardiac anatomy information of at least a portion of a heart of the object; determining a first blood parameter of the object based on the specific data of the object and the first model of the object; determining a second model of the object, the second model comprising a configuration of a grafted vessel of the object; determining a second blood parameter of the object based on the specific data of the object and the second model of the object; and determining a quantification result of the object based on the first blood parameter and the second blood parameter.

In some embodiments, the specific data of the object may include at least one of a systolic pressure, a diastolic pressure, a heart rate, a cardiac output, a blood property, a gender, an age, a height, a weight, a medical history, smoking, diabetes, hypertension, or imaging data of the object In some embodiments, the first blood parameter of the object may include at least one of a blood pressure, a blood flow velocity, a blood flow flux, or a wall shear stress at each of one or more points or each of one or more regions of the first model of the object or one or more computed results determined based on at least one of the blood pressure, the blood flow velocity, the blood flow flux, or the wall shear stress.

In some embodiments, the second blood parameter of the object may include at least one of a blood pressure, a blood flow velocity, a blood flow flux, or a wall shear stress at each of one or more points or each of one or more regions of the second model of the object or one or more computed results determined based on at least one of the blood pressure, the blood flow velocity, the blood flow flux, or the wall shear stress.

In some embodiments, the determining the first model of the object may include: obtaining imaging data of the object acquired by scanning the object; and determining the first model of the object by performing, based on the imaging data, an image segmentation with respect to the at least a portion of the heart.

In some embodiments, the grafted vessel may include a virtual grafted vessel. The determining the second model of the object may include: determining a configuration of the virtual grafted vessel of the object based on a vessel determination model; and determining the second model of the object by combining the first model and the configuration of the virtual grafted vessel.

In some embodiments, the determining the configuration of the virtual grafted vessel of the object based on the vessel determination model may include: obtaining feature information of the virtual grafted vessel of the object; and determining the configuration of the virtual grafted vessel by inputting the specific data of the object, the feature information of the virtual grafted vessel, and the first model into the vessel determination model.

In some embodiments, the feature information of the virtual grafted vessel may include at least one of one or more anastomosis positions between the virtual grafted vessel and a coronary artery, a length of the virtual grafted vessel, a diameter of the virtual grafted vessel at one or more points, a length of the virtual grafted vessel between the one or more anastomosis positions, an angle between the virtual grafted vessel and an aorta at one of the one or more anastomosis positions, or an angle between the virtual grafted vessel and a coronary artery at one of the one or more anastomosis positions.

In some embodiments, the vessel determination model may be determined by a training process including: obtaining a plurality of training samples, each of the plurality of training samples comprising training specific data of a training object, a training first model of the training object, training feature information of a training grafted vessel of the object; and generating the vessel determination model by training a preliminary vessel determination model based on the plurality of training samples.

In some embodiments, the grafted vessel may include an actual grafted vessel. The determining the second model of the object may include: obtaining imaging data of the object acquired by scanning the object; and determining the second model of the object by performing, based on the imaging data, an image segmentation with respect to the at least a portion of the heart and the actual grafted vessel.

In some embodiments, the grafted vessel may include an actual grafted vessel. The determining the first model of the object may include: determining a configuration of the actual grafted vessel based on the second model of the object; and determining the first model of the object by removing the configuration of the actual grafted vessel from the second model.

In some embodiments, the determining the configuration of the actual grafted vessel based on the second model of the object may include: determining the configuration of the actual grafted vessel based on the feature information of the actual grafted vessel using a second vessel determination model.

In some embodiments, the determining the first blood parameter of the object based on the specific data of the object and the first model of the object may include: meshing the first model of the object; and determining the first blood parameter of the object based on the specific data of the object and the meshed first model.

In some embodiments, the determining the second blood parameter of the object based on the specific data of the object and the second model of the object may include: meshing the second model of the object; and determining the second blood parameter of the object based on the specific data of the object and the meshed second model.

In some embodiments, the determining the quantification result of the object based on the first blood parameter and the second blood parameter may include: determining a difference between the first blood parameter and the second blood parameter; and determining the quantification result of the object based on the difference.

In some embodiments, the determining the quantification result of the object based on the first blood parameter and the second blood parameter may include: determining a ratio between the first blood parameter and the second blood parameter; and determining the quantification result of the object based on the ratio.

In some embodiments, the grafted vessel may include a virtual grafted vessel. The determining the quantification result of the object based on the first blood parameter and the second blood parameter may include: determining whether the quantification result satisfies a predetermined condition; in response to determining that the quantification result fails to satisfy the predetermined condition, adjusting feature information of the virtual grafted vessel; determining, using a vessel determination model, an adjusted configuration of an adjusted virtual grafted vessel based on the specific data of the object and the adjusted feature information; determining an adjusted second model by combining the adjusted configuration of the adjusted virtual grafted vessel and the first model of the object; determining an adjusted second blood parameter based on the adjusted second model and the specific data of the object; and determining an adjusted quantification result of the object based on the first blood parameter and the adjusted second blood parameter.

In some embodiments, the grafted vessel may include an actual grafted vessel. The determining the quantification result of the object based on the first blood parameter and the second blood parameter may include: determining whether the quantification result satisfies a predetermined condition; and determining a probability of a clinical event of the object based on whether the quantification result satisfies a predetermined condition.

According to some embodiments of the present disclosure, a method may be implemented on a computing device having at least one processor, and at least one storage device. The method may include: acquiring specific data of an object; determining a first model of the object, the first model comprising cardiac anatomy information of at least a portion of a heart of the object; determining a first blood parameter of the object based on the specific data of the object and the first model of the object; determining a second model of the object, the second model comprising a configuration of a grafted vessel of the object; determining a second blood parameter of the object based on the specific data of the object and the second model of the object; and determining a quantification result of the object based on the first blood parameter and the second blood parameter.

According to some embodiments of the present disclosure, a non-transitory computer readable medium may include at least one set of instructions. When executed by at least one processor of a computing device, the at least one set of instructions may cause the at least one processor to effectuate a method comprising: acquiring specific data of an object; determining a first model of the object, the first model comprising cardiac anatomy information of at least a portion of a heart of the object; determining a first blood parameter of the object based on the specific data of the object and the first model of the object; determining a second model of the object, the second model comprising a configuration of a grafted vessel of the object; determining a second blood parameter of the object based on the specific data of the object and the second model of the object; and determining a quantification result of the object based on the first blood parameter and the second blood parameter.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for blood parameter assessment according to some embodiments of the present disclosure;

DETAILED DESCRIPTION

Figure 1:
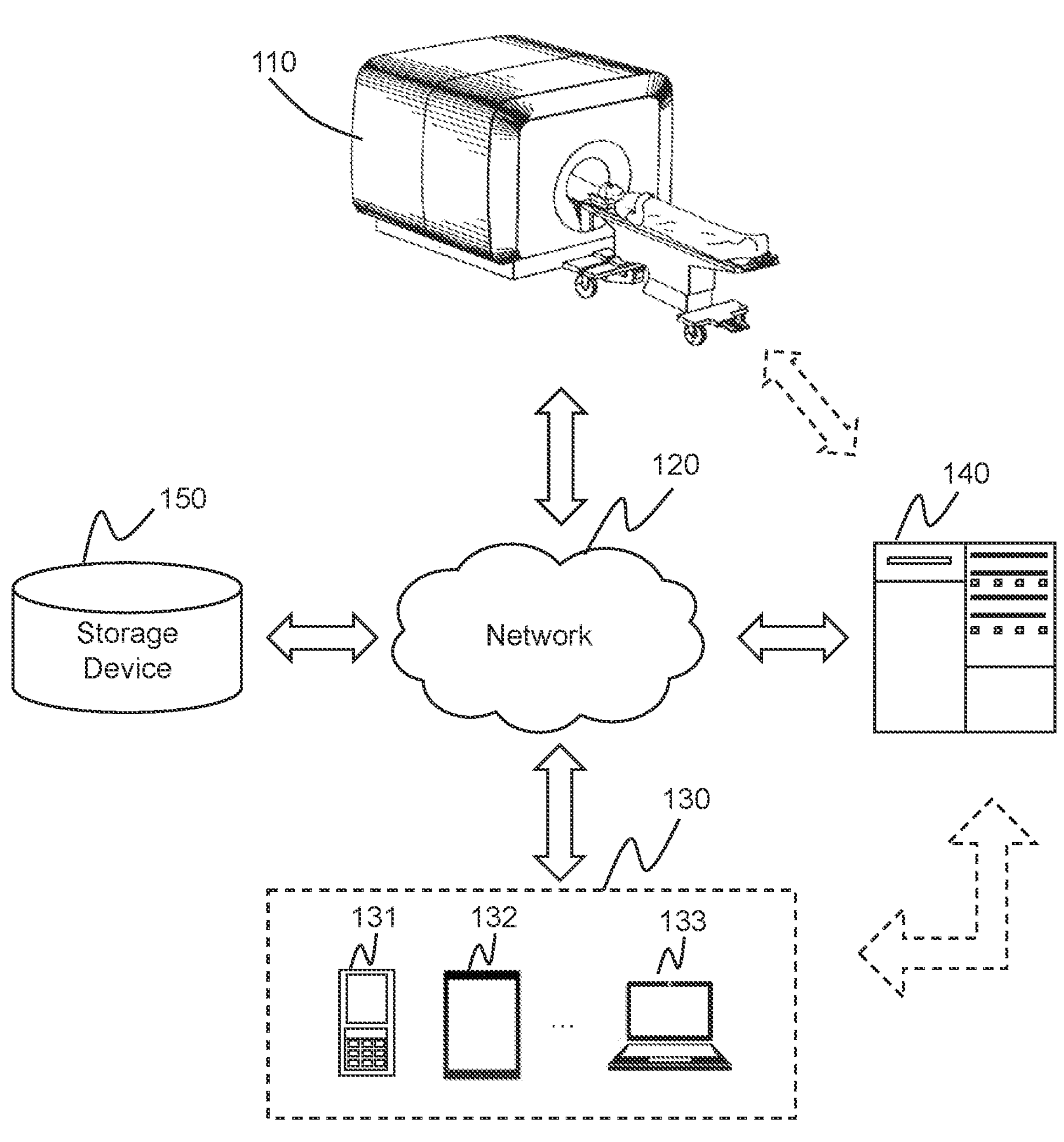
FIG. 1 is a schematic diagram illustrating an exemplary blood parameter assessment system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be understood that the terms "system," "unit," "module," and/or "block" used herein are one method to distinguish different components, elements, parts, sections or assemblies of different levels in ascending order. However, the terms may be displaced by another expression if they achieve the same purpose.

The modules (or units, blocks, units) described in the present disclosure may be implemented as software and/or hardware modules and may be stored in any type of non-transitory computer-readable medium or other storage devices. In some embodiments, a software module may be compiled and linked into an executable program. It will be appreciated that software modules can be callable from other modules or from themselves, and/or can be invoked in response to detected events or interrupts. Software modules configured for execution on computing devices can be provided on a computer readable medium or as a digital download (and can be originally stored in a compressed or installable format that requires installation, decompression, or decryption prior to execution). Such software code can be stored, partially or fully, on a memory device of the executing computing device, for execution by the computing device. Software instructions can be embedded in a firmware, such as an EPROM. It will be further appreciated that hardware modules (e.g., circuits) can be included in connected or coupled logic units, such as gates and flip-flops, and/or can be included in programmable units, such as programmable gate arrays or processors. The modules or computing device functionality described herein are preferably implemented as hardware modules, but can be software modules as well. In general, the modules described herein refer to logical modules that can be combined with other modules or divided into units despite their physical organization or storage.

Certain terminology has been used to describe embodiments of the present disclosure. For example, the terms "one embodiment," "an embodiment," and/or "some embodiments" mean that a particular feature, structure or characteristic described in connection with the embodiment is in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

In the present disclosure, a representation of an object (e.g., a patient or a portion thereof) in imaging data (e.g., an image) may be referred to as "object" for brevity. For instance, a representation of an organ, tissue, or a region of interest (ROI) (e.g., a heart, a vessel) in the imaging data may be referred to as the organ, tissue, or ROI, for brevity. Further, the imaging data including a representation of an object, or a portion thereof, may be referred to as the imaging data of the object, or a portion thereof, or the imaging data including the object, or a portion thereof, for brevity. Still further, an operation performed on the representation of the object, or a portion thereof, in the imaging data may be referred to as an operation performed on the object, or a portion thereof, for brevity. For instance, a segmentation of a portion of the imaging data including a representation of the object, or a portion thereof from the imaging data may be referred to as a segmentation of the object, or a portion thereof for brevity.

FIG. 1 is a schematic diagram illustrating an exemplary blood parameter assessment system according to some embodiments of the present disclosure. As illustrated, the blood parameter assessment system 100 may include an imaging device 110, a network 120, a terminal 130, a processing device 140, and a storage device 150. The components of the blood parameter assessment system 100 may be connected in one or more of various ways. Merely by way of example, as illustrated in FIG. 1, the imaging device 110 may be connected to the processing device 140 through the network 120. As another example, the imaging device 110 may be connected to the processing device 140 directly (as indicated by the bi-directional arrow in dotted lines linking the imaging device 110 and the processing device 140). As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the terminal 130 and the processing device 140) or through the network 120.

The imaging device 110 may scan an object located within its detection region and generate imaging data relating to the object. In the present disclosure, "subject" and "object" are used interchangeably. In some embodiments, the imaging data may be two-dimensional (2D) imaging data, three-dimensional (3D) imaging data, four-dimensional (4D) imaging data, or the like, or any combination thereof. Merely by way of example, the object may include a patient, a man-made object, etc. As another example, the object may include a specific portion, organ, and/or tissue of a patient. For example, the object may include the heart, a vessel, the head, the brain, the neck, the torso, a shoulder, an arm, the thorax, the stomach, soft tissue, a knee, a foot, or the like, or any combination thereof, or a patient. In some embodiments, the imaging device 110 may include a digital subtraction angiography (DSA) device, a magnetic resonance angiography (MRA) device, a computed tomography angiography (CTA) device, a computed tomography (CT) imaging device, a magnetic resonance imaging (MRI), a positron emission tomography (PET) imaging device, a single photon emission computed tomography (SPECT) imaging device, an ultrasound imaging device, or the like, or any combination thereof.

The network 120 may include any suitable network that can facilitate the exchange of information and/or data for the blood parameter assessment system 100. In some embodiments, one or more components of the blood parameter assessment system 100 (e.g., the imaging device 110, the terminal 130, the processing device 140, or the storage device 150) may communicate information and/or data with one or more other components of the blood parameter assessment system 100 via the network 120. In some embodiments, the network 120 may be any type of wired or wireless network, or a combination thereof.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the terminal 130 may remotely operate the imaging device 110 and/or the processing device 140. In some embodiments, the terminal 130 may operate the imaging device 110 and/or the processing device 140 via a wireless connection. In some embodiments, the terminal 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the imaging device 110, the terminal 130, and/or the storage device 150. For example, the processing device 140 may determine a blood parameter of the object based on specific data of the object and a model (e.g., a first model, a second model) of the object. In some embodiments, the processing device 140 may be a single server or a server group. The server group may be centralized or distributed. In some embodiments, the processing device 140 may be local or remote. In some embodiments, the processing device 140 may be implemented on a cloud platform.

The storage device 150 may store data and/or instructions. In some embodiments, the storage device 150 may store data obtained from the imaging device 110, the terminal 130 and/or the processing device 140. In some embodiments, the storage device 150 may store data and/or instructions that the processing device 140 may execute or use to perform exemplary methods described in the present disclosure. For example, the storage device 150 may store instructions that the processing device 140 may execute to determine a blood parameter of the object based on specific data of the object and a model (e.g., a first model, a second model) of the object. In some embodiments, the storage device 150 may include a mass storage device, a removable storage device, a volatile read-and-write memory, a read-only memory (ROM), or the like, or any combination thereof. In some embodiments, the storage device 150 may be implemented on a cloud platform.

In some embodiments, the storage device 150 may be connected to the network 120 to communicate with one or more components of the blood parameter assessment system 100 (e.g., the imaging device 110, the processing device 140, the terminal 130, etc.). One or more components of the blood parameter assessment system 100 may access the data or instructions stored in the storage device 150 via the network 120. In some embodiments, the storage device 150 may be part of the processing device 140.

Figure 2:
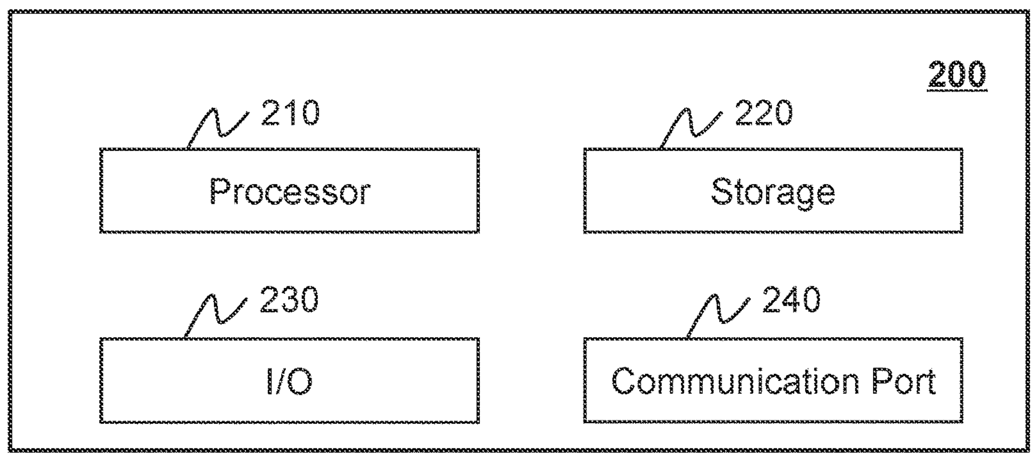
FIG. 2 is a schematic diagram illustrating hardware and/or software components of an exemplary computing device according to some embodiments of the present disclosure.

In some embodiments, the blood parameter assessment system 100 may further include one or more power supplies (not shown in FIG. 1) operably connected to one or more components of the blood parameter assessment system 100 (e.g., the Imaging device 110, the processing device 140, the terminal 130, the storage device 150, etc.). FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. For example, the processor 210 may obtain imaging data of the object from the storage device 150 and/or a terminal 130. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The storage 220 may store data/information obtained from the imaging device 110, the terminal 130, the storage device 150, or any other component of the blood parameter assessment system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 for determining a blood parameter of the object based on specific data of the object and a model (e.g., a first model, a second model) of the object.

The I/O 230 may input or output signals, data, or information. In some embodiments, the I/O 230 may enable user interaction with the processing device 140. In some embodiments, the I/O 230 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
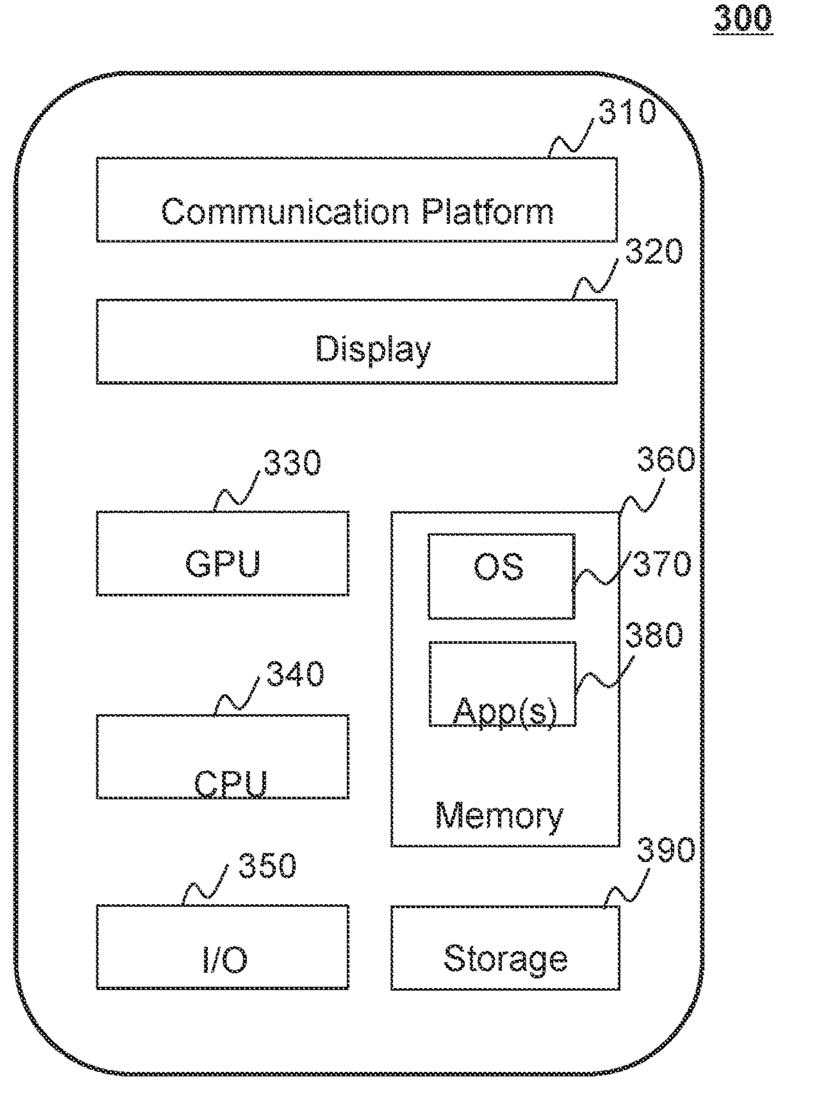
FIG. 3 is a schematic diagram illustrating hardware and/or software components of an exemplary mobile device according to some embodiments of the present disclosure.

FIG. 3 is a schematic diagram illustrating exemplary hardware and/or software components of a mobile device on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to blood parameter assessment or other information from the processing device 140. User interactions with the information stream may be achieved via the I/O 350 and provided to the processing device 140 and/or other components of the Blood parameter assessment system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood parameter assessment as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4A:
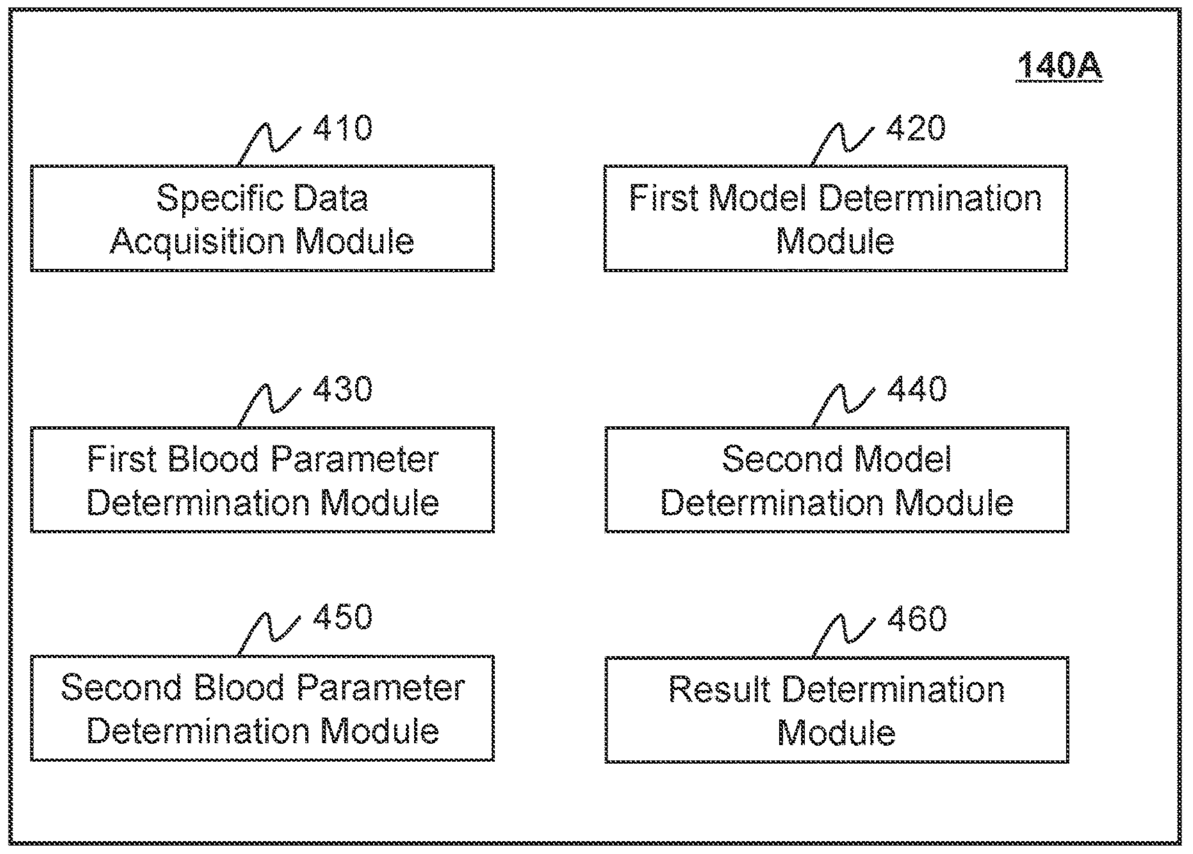
FIG. 4A is a block diagram illustrating an exemplary processing device according to some embodiments of the present disclosure.
Figure 4B:
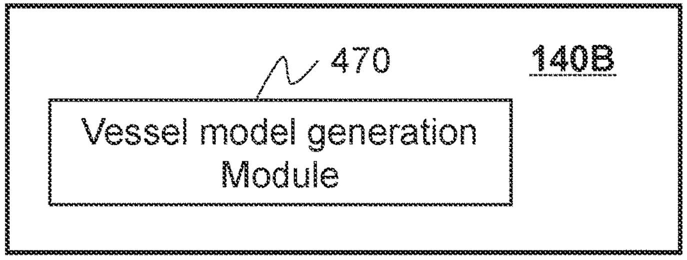
FIG. 4B is a block diagram illustrating an exemplary processing device according to some embodiments of the present disclosure.

FIG. 4A and FIG. 4B are schematic block diagrams illustrating exemplary processing devices according to some embodiments of the present disclosure. In some embodiments, the processing device 140A may be configured to determine a quantification result of an object based on a first blood parameter and a second blood parameter of the object. The processing device 140B may be configured to generate a vessel determination model by training a preliminary vessel determination model based on a plurality of training samples. For illustration purposes, the processing devices 140A and 140B may respectively be implemented on the computing device 200 as illustrated in FIG. 2 or the CPU 340 as illustrated in FIG. 3. In some embodiments, the processing device 140A and the processing device 140B may be both implemented on the processing device 140 as illustrated in FIG. 1. In some embodiments, the processing device 140A may be implemented on the processing device 140 as illustrated in FIG. 1, while the processing device 140B may be implemented on a processing device of a manufacturer or vendor who provides and/or maintains the vessel determination model.

The processing device 140A may include a specific data acquisition module 410, a first model determination module 420, a first blood parameter determination module 430, a second model determination module 440, a second blood parameter determination module 450, and a result determination module 460.

Figure 5:
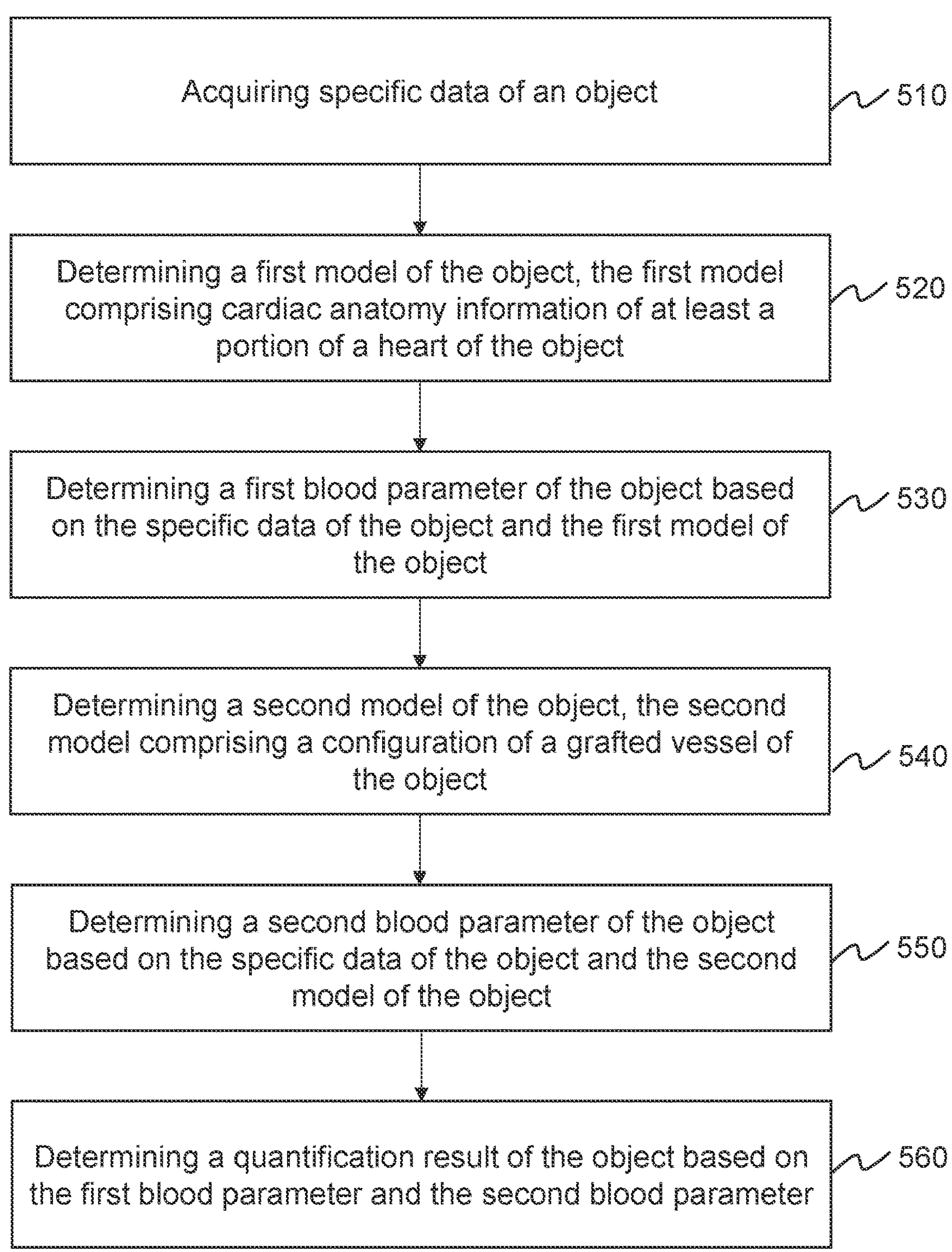
FIG. 5 is a flowchart illustrating an exemplary blood parameter assessment process according to some embodiments of the present disclosure.

The specific data acquisition module 410 may be configured to acquire specific data of an object, more descriptions of which are found elsewhere in the present disclosure, for example, FIG. 5 and/or the descriptions thereof.

The first model determination module 420 may be configured to determine a first model of the object, more descriptions of which are found elsewhere in the present disclosure, for example, FIG. 5 and/or the descriptions thereof.

The first blood parameter determination module 430 may be configured to determine the first blood parameter of the object based on the specific data of the object and the first model of the object, more descriptions of which are found elsewhere in the present disclosure, for example, FIG. 5 and/or the descriptions thereof.

The second model determination module 440 may be configured to determine a second model of the object, the second model comprising a configuration of a grafted vessel of the object, more descriptions of which are found elsewhere in the present disclosure, for example, FIG. 5 and/or the descriptions thereof.

The second blood parameter determination module 450 may be configured to determine the second blood parameter of the object based on the specific data of the object and the second model of the object, more descriptions of which are found elsewhere in the present disclosure, for example, FIG. 5 and/or the descriptions thereof.

Figure 7:
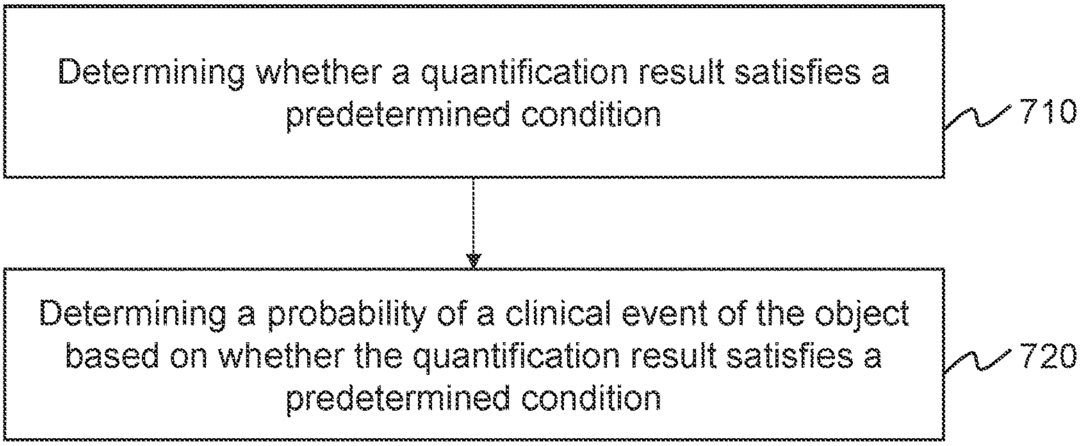
FIG. 7 is a flowchart illustrating an exemplary process for blood parameter assessment according to some embodiments of the present disclosure.

The result determination module 460 may be configured to determine a quantification result of the object based on the first blood parameter and the second blood parameter, more descriptions of which are found elsewhere in the present disclosure, for example, FIGS. 5-7, and/or the descriptions thereof.

The processing device 140B may include a vessel model generation module 470. The vessel model generation module 470 may be configured to generate the vessel determination model by training the preliminary vessel determination model based on the plurality of training samples, more descriptions of which are found elsewhere in the present disclosure, for example, FIG. 8 and/or the descriptions thereof.

The modules in the processing device 140A or the processing device 140B may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

FIG. 5 is a flowchart illustrating an exemplary blood parameter assessment process according to some embodiments of the present disclosure. In some embodiments, process 500 may be executed by the blood parameter assessment system 100. For example, the process 500 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules of the processing device 140A illustrated in FIG. 4A) may execute the set of instructions and may accordingly be directed to perform the process 500. The operations of the illustrated process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 140 (e.g., the specific data acquisition module 410) may acquire specific data of an object. For example, the specific data of the object may include a systolic pressure, a diastolic pressure, a heart rate, a cardiac output, a blood property (e.g., an amount, a blood volume, a viscosity, a specific gravity, pH, a temperature, an osmotic pressure, a color, a blood type), a gender, an age, a height, a weight, a disease, a medical history, smoking, diabetes, hypertension, imaging data of the object, or the like, or any combination thereof.

In some embodiments, the object may have a heart disease (e.g., a coronary artery disease (CAD)) and need to undergo an interventional therapy (e.g., a bypass surgery). In some embodiments, the specific data of the object may include specific data (also referred to as preoperative specific data) of the object before the interventional therapy is performed on the object, specific data (also referred to as postoperative specific data) of the object after the interventional therapy is performed on the object, specific data of the object during the interventional therapy of the object, or the like, or any combination thereof.

In some embodiments, at least a portion of the specific data of the object may be acquired using a medical instrument. For example, the systolic pressure, the diastolic pressure, and/or the heart rate of the object may be acquired using a sphygmomanometer. In some embodiments, at least a portion of the specific data of the object may be acquired from the medical history (e.g., consultation information, diagnostic information) of the object, an imaging protocol of the object, etc.

In some embodiments, the processing device 140 may obtain at least a portion of the specific data from a component (e.g., the imaging device 110, the terminal 130, the storage device 150) of the blood parameter assessment system 100, a source external to the blood parameter assessment system 100, etc. In some embodiments, the processing device 140 may determine at least a portion of the specific data by processing information (e.g., imaging data of the object) obtained from a component of the blood parameter assessment system 100, a source external to the blood parameter assessment system 100, etc.

In 520, the processing device 140 (e.g., the first model determination module 420) may determine a first model of the object. The first model of the object may include cardiac anatomy information of at least a portion of the heart of the object. In some embodiments, the first model of the object may include cardiac anatomy information of the whole heart of the object. In some embodiments, the first model of the object may include cardiac anatomy information of only a portion of the heart (not the whole heart) of the object. For example, the portion of the heart of the object may include a coronary artery of the heart, the aorta of the heart, a chamber (e.g., a ventricle, an atria) of the heart, the myocardium of the heart, the epicardium of the heart, the endocardium of the heart, or the like, or any combination thereof.

In some embodiments, the cardiac anatomy information of the at least a portion of the heart of the object may include a configuration (e.g., a 3D configuration, a 2D configuration) of the at least a portion of the heart, etc. In some embodiments, the first model (also referred to as a preoperative model) may include the cardiac anatomy information of the object before the interventional therapy is performed on the object. Accordingly, the first model may include a configuration (e.g., a 3D configuration, a 2D configuration) of the at least a portion of the heart, etc., before the interventional therapy is performed on the object.

In some embodiments, the processing device 140 may obtain imaging data of the object acquired by scanning the object. In some embodiments, the processing device 140 may determine the first model of the object by performing, based on the imaging data, an image segmentation with respect to the at least a portion of the heart. The image segmentation used herein may refer to a segmentation of a representation of the at least a portion of the heart from the imaging data. The processing device 140 may perform the image segmentation based on a segmentation technique. For example, the segmentation technique may include a region-based segmentation technique, an edge-based segmentation technique, a wavelet transform segmentation technique, a mathematical morphology segmentation technique, a genetic algorithm-based segmentation technique, or the like, or a combination thereof.

In some embodiments, the processing device 140 may preprocess the imaging data and then perform the image segmentation based on the preprocessed imaging data. In some embodiments, the processing device 140 may preprocess the imaging data based on an image enhancement technique. For example, the image enhancement technique may include a histogram equalization technique, a gray world technique, an automatic white balance technique, an automatic color equalization technique, a deep learning technique, or the like, or any combination thereof.

In some embodiments, the processing device 140 may determine the first model of the object based on the imaging data using a machine learning model (e.g., a neural network model). For example, the machine learning model may include a convolutional neural network (CNN) model, a recurrent neural network (RNN) model, a long short term memory (LSTM) network model, a fully convolutional neural network (FCN) model, a generative adversarial network (GAN) model, a Hopfield model, a dilated convolution model, a conditional random fields as recurrent neural networks (CRFasRNN) model, or the like, or any combination thereof.

In some embodiments, the processing device 140 may obtain the imaging data from the imaging device 110, the storage device 150 of the blood parameter assessment system 100, an external source connected to the blood parameter assessment system 100, etc.

In 530, the processing device 140 (e.g., the first blood parameter determination module 430) may determine a first blood parameter of the object based on the specific data of the object and the first model of the object. The processing device 140 may determine the first blood parameter (also referred to as a preoperative blood parameter) of the object based on the preoperative specific data of the object and the first model of the object.

In some embodiments, the first blood parameter of the object may include a blood pressure, a blood flow velocity, a blood flow flux, a wall shear stress, a fractional flow reserve (FFR) value at each of one or more points or locations or each of one or more regions of the first model of the object, one or more computed results determined based on at least one of the blood pressure, the blood flow velocity, the blood flow flux, or the wall shear stress, or the like, or any combination thereof. In some embodiments, the point, location, or region of the first model of the object may include an inlet of a vessel, an outlet of the vessel, a point or region near the inlet of the vessel, a point or region near the outlet of the vessel, a point or region upstream of the vessel, a point or region downstream of the vessel, a point or region of a branch of the vessel, a point or region where a vessel becomes narrower, a point or region where the blood flow velocity is lower than a threshold, or the like, or any combination thereof. The vessel used herein may include a pathological vessel, a vessel upstream of the pathological vessel, a vessel downstream of the pathological vessel, etc. For example, the pathological vessel may include a pathological coronary artery, a pathological aorta, etc.

In some embodiments, the processing device 140 may designate a blood parameter (e.g., a wall shear stress) of a first point near a second point as the first blood parameter, in which the second point is upstream of the pathological vessel. A distance between the first point and the second point may be smaller than a distance threshold. In some embodiments, the processing device 140 may designate a blood parameter (e.g., a wall shear stress) of a third point near a fourth point downstream of the phycological vessel as the first blood parameter. A distance between the third point and the fourth point may be smaller than a second distance threshold. The second distance threshold may be the same as or different from the distance threshold. In some embodiments, the processing device 140 may designate a difference between the blood parameter of the first point and the blood parameter of the third point as the first blood parameter. In some embodiments, the processing device 140 may determine one or more blood parameters (e.g., a wall shear stress) of one or more points of a cross-section of a vessel upstream of the pathological vessel and determine the first blood parameter based on the one or more blood parameters of the one or more points. For example, the processing device 140 may designate an average, a medium value, etc., of the one or more blood parameters as the first blood parameter. In some embodiments, the processing device 140 may determine one or more blood parameters (e.g., a wall shear stress) of one or more points of a cross-section of a vessel downstream of the pathological vessel and determine the first blood parameter based on the one or more blood parameters. For example, the processing device 140 may designate an average, a medium value, etc., of the one or more blood parameters as the first blood parameter.

In some embodiments, the processing device 140 may determine the first blood parameter of the object based on the specific data of the object and the first model of the object using a blood parameter determination model. In some embodiments, the blood parameter determination model may be a machine learning model. In some embodiments, the blood parameter determination model may be generated by training a preliminary blood parameter determination model (e.g., a machine learning model) using a plurality of training samples. Each of the plurality of training samples may include training specific data of a training object and a training first model of the training object. In some embodiments, the training specific data of the training object and the training first model of the training object may be the same as or similar to the specific data of the object and the training first model of the training object, respectively.

In some embodiments, the processing device 140 may mesh the first model of the object to generate a meshed first model. The meshing of the first model of the object may be performed based on a meshing technique. For example, the meshing technique may include a computer-aided design (CAD)—based technique, an image-based on technique, etc. The meshing of the first model of the object may facilitate the application of a computational fluid dynamics (CFD) technique in determining one or more parameters, including, e.g., one or more blood parameters, as described elsewhere in the present disclosure.

In some embodiments, the processing device 140 may determine the first blood parameter of the object based on the specific data of the object and the meshed first model. The processing device 140 may determine a boundary condition of the meshed first model of the object based on the specific data. In some embodiments, the boundary condition may include information at one or more points or locations of the boundary of the meshed first model including, e.g., at an inlet of a vessel in the meshed first model at, an outlet of a vessel in the meshed first model, at a vessel wall in the meshed first model, etc. The boundary condition may include at least one of a pressure, a velocity, a mass flow, a resistance, or a derivative thereof. The boundary condition may be determined based on one or more parameters, e.g., the length of a vessel, or a portion thereof; the area, the radius, and/or the diameter of a cross-section of the vessel; the thickness of the vessel wall of a vessel, or a portion thereof; the centerline of a vessel, or a portion thereof; etc. In some embodiments, the processing device 140 may determine geometric information of an outlet of a vessel of interest (e.g., a coronary artery) of the object based on the specific data and/or the meshed first model of the object. The processing device 140 may determine, based on the geometric information of the outlet of the vessel of interest of the object, an impedance (or resistance) at the outlet of the vessel of interest of the object. The processing device 140 may determine the boundary condition based on the specific data and/or the impedance at the outlet of the vessel of interest of the object. For example, the processing device 140 may designate the specific data and/or the impedance at the outlet of the vessel of interest of the object as the boundary condition. Further, the processing device 140 may determine the first blood parameter by solving, based on the boundary condition, the meshed first model using a computational algorithm, e.g., SIMPLE, PISO, PIMPLE, etc.

In some embodiments, the processing device 140 may designate a blood parameter at a cross-section of a vessel described in the first model as the first blood parameter. For instance, the processing device 140 may determine one or more blood parameters of one or more meshes of the cross-section of the vessel, and designate a sum or an average of the one or more blood parameters as the blood parameter at the cross-section of the vessel in the first model.

In 540, the processing device 140 (e.g., the second model determination module 440) may determine a second model of the object. In some embodiments, the interventional therapy may include a bypass surgery in which a healthy vessel (or referred to as a grafted vessel) is connected to the object so as to form a new pathway that redirects blood around the pathological vessel (e.g., a pathological coronary artery) of the object. In some embodiments, the second model (also referred to as a postoperative model) may include a configuration of the grafted vessel of the object after the interventional therapy is performed on the object. In some embodiments, the second model may also include the cardiac anatomy information of the at least a portion of the heart of the object; that is, the second model may include the configuration of the grafted vessel of the object and at least a portion of the first model of the object.

In some embodiments, the grafted vessel may include a virtual grafted vessel. In some embodiments, the processing device 140 may determine, based on a vessel determination model, a configuration (or visualization) of the virtual grafted vessel. The processing device 140 may determine the second model (also referred as a virtual postoperative model) of the object by combining the first model and the virtual grafted vessel. In some embodiments, the processing device 140 may combine the first model and the virtual grafted vessel based on a combination algorithm. For instance, for a pixel or voxel of the second model, the pixel or voxel value may be determined based on a pixel or voxel value of a corresponding pixel or voxel of the first model and the pixel or voxel value of a corresponding pixel or voxel the virtual grafted vessel. As used herein, a pixel or voxel of model A is considered corresponding to a pixel or voxel of model B if the pixel or voxel of model A and the pixel or voxel of model B represent a same physical point (e.g., a physical point of the object or an environment surrounding the object that is included in model A and model B; model A or model B may include the first model, the second model, or the virtual grafted vessel. Exemplary combination algorithms may include a weighted average algorithm (e.g., a stepwise weighted average algorithm), a simple maximum algorithm, a simple minimum algorithm, a simple average algorithm, a principal component analysis (PCA) algorithm, a discrete wavelet transform (DWT) algorithm, or the like, or any combination thereof.

In some embodiments, the processing device 140 may obtain feature information of the virtual grafted vessel of the object. In some embodiments, the feature information of the virtual grafted vessel of the object may include one or more anastomosis positions between the virtual grafted vessel and a coronary artery, a length of the virtual grafted vessel, a diameter of the virtual grafted vessel at one or more points, a length of the virtual grafted vessel between the one or more anastomosis positions, an angle between the virtual grafted vessel and an aorta at one of the one or more anastomosis positions, an angle between the virtual grafted vessel and a coronary artery at one of the one or more anastomosis positions, or the like, or any combination thereof.

In some embodiments, the feature information of the virtual grafted vessel may be determined automatically, semi-automatically, or manually. In some embodiments, the feature information of the virtual grafted vessel may be determined based on the specific data of the object. In some embodiments, the feature information of the virtual grafted vessel may be determined based on historical feature information of a historical grafted vessel that is grafted to another object having similar feature information compared to the object. For example, the historical feature information of the historical grafted vessel may be designated as the feature information of the virtual grafted vessel.

In some embodiments, the processing device 140 may determine, using the vessel determination model, the configuration of the virtual grafted vessel based on the feature information of the virtual grafted vessel and the specific data of the object. In some embodiments, the processing device 140 may determine the configuration of the virtual grafted vessel by inputting the specific data of the object, the feature information of the virtual grafted vessel, and the first model into the vessel determination model. In some embodiments, the vessel determined model may be determined by a training process. The training process may include obtaining a plurality of training samples and generating the vessel determination model by training a preliminary vessel determination model (e.g., a machine learning model) based on the plurality of training samples. More descriptions of the generation of the vessel determination model may be found elsewhere in the present disclosure, for example, FIG. 8 and/or the descriptions thereof.

In 550, the processing device 140 (e.g., the second blood parameter determination module 450) may determine a second blood parameter of the object based on the specific data of the object and the second model of the object. In some embodiments, the processing device 140 may determine the second blood parameter (also referred to as a postoperative blood parameter) of the object based on the postoperative specific data of the object and the second model of the object.

In some embodiments, the second blood parameter of the object may include a blood pressure, a blood flow velocity, a blood flow flux, a wall shear stress, a fractional flow reserve (FFR) value at each of one or more points or locations or each of one or more regions of the second model of the object or one or more computed results determined based on at least one of the blood pressure, the blood flow velocity, the blood flow flux, or the wall shear stress, or the like, or any combination thereof. In some embodiments, the point, location, or region of the second model of the object may include an inlet of a vessel, an outlet of the vessel, a point or region upstream of the vessel, a point or region downstream of the vessel, a point or region of a branch of the vessel, a point or region where a vessel becomes narrower, a point or region where the blood flow velocity is lower than a threshold, or the like, or any combination thereof. The second blood parameter may be determined based on parameters at the same or similar point, location, or region of the second model to facilitate the comparison and/or assessment of the object before and after the interventional therapy. The second blood parameter may be determined in a same or similar manner as the first blood parameter as described in connection with 530, the description of which is not repeated.

Merely by way of example, the processing device 140 may determine the second blood parameter of the object based on the specific data of the object and the second model of the object using a second blood parameter determination model. The second blood parameter determination model may be the same as or different from the blood parameter determination model illustrated in 530. In some embodiments, the second blood parameter determination model may be a machine learning model. In some embodiments, the second blood parameter determination model may be generated by training a preliminary blood parameter determination model (e.g., a machine learning model) using a plurality of training samples. Each of the plurality of training samples may include training specific data of a training object and a training second model of the training object. In some embodiments, the training specific data of the training object and the training second model of the training object may be the same as or similar to the specific data of the object and the second model of the object, respectively, more descriptions of which are not repeated.

In some embodiments, the processing device 140 may determine the second blood parameter of the object based on the specific data of the object and a meshed second model using a computational fluid dynamics technique.

In some embodiments, the processing device 140 may designate a blood parameter at a cross-section of a vessel described in the second model as the second blood parameter. For example, the processing device 140 may determine one or more blood parameters of one or more meshes of the cross-section of the vessel, and designate a sum or an average of the one or more blood parameters as the blood parameter at the cross-section of the vessel of the second model.

In 560, the processing device 140 (e.g., the result determination module 460) may determine a quantification result of the object based on the first blood parameter and the second blood parameter. In some embodiments, the quantification result of the object may include the first blood parameter and/or the second blood parameter.

In some embodiments, the processing device 140 may determine a difference between the first blood parameter and the second blood parameter. Merely by way of example, the first blood parameter and the second blood parameter may include the FFR value, the blood flow flux, the pressure at an inlet or an outlet of a vessel of the object before and after the interventional therapy, respectively. The processing device 140 may determine the quantification result of the object based on the difference. In some embodiments, the quantification result may include the difference. In some embodiments, the qualification result of the object may include the difference expressed in an absolute value. For instance, the difference between the first blood parameter and the second blood parameter may be determined by subtracting the FFR value of the second blood parameter from the FFR value of the first blood parameter.

In some embodiments, the quantification result of the object may include the difference expressed as a percentage. For instance, the difference between the first blood parameter and the second blood parameter may include a percentage difference between FFR values of the first blood parameter and the second blood parameter.

In some embodiments, the processing device 140 may determine a ratio between the first blood parameter and the second blood parameter. The processing device 140 may determine the quantification result of the object based on the ratio. In some embodiments, the quantification result may include the ratio.

In some embodiments, the quantification result may be used to evaluate the efficacy of the interventional therapy on the object. The efficacy of the interventional therapy may be evaluated by determining whether the second blood parameter of the object is within a predetermined parameter range (e.g., a clinical reference range), whether a clinical event of the object occurs after the interventional therapy is performed, whether a probability of the clinical event is smaller than a probability threshold (e.g., 50%, 75%), etc. In some embodiments, the clinical event may include stenosis of the grafted vessel, spasm of the grafted vessel, recurrent myocardial ischemia, myocardial infarction, vessel revascularization, etc.

In some embodiments, the quantification result may include a first quantification result determined based on the preoperative blood parameter and a virtual postoperative blood parameter. The processing device 140 may determine the virtual postoperative blood parameter based on the virtual postoperative model and the specific data of the object. The first quantification result may be used to evaluate the efficacy of a virtual interventional therapy (e.g., a planned interventional therapy) including grafting the virtual grafted vessel to the object, facilitating an adjustment of the virtual interventional therapy to improve a blood supply of the object (e.g., an outlet of a pathological vessel thereof) and/or assisting an operator (e.g., a doctor) in clinical decision-making for an actual interventional therapy of the object in a non-invasive manner. More descriptions of the utilization of the first qualification result may be found elsewhere in the present disclosure. See, for example, FIG. 6 and/or the descriptions thereof.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the processing device 140 may obtain the first model and the second model in a manner different from that described in 510-540. In some embodiments, the grafted vessel may include an actual grafted vessel. In some embodiments, the processing device 140 may obtain imaging data (also referred to as postoperative imaging data) of the object acquired by scanning the object after the interventional therapy is actually performed. The processing device 140 may determine the second model (also referred to as an actual postoperative model) of the object by performing, based on the postoperative imaging data, an image segmentation with respect to the at least a portion of the heart and an actual grafted vessel. The image segmentation used herein may refer to a segmentation of a representation of the at least a portion of the heart and the actual grafted vessel from the postoperative imaging data. The processing device 140 may perform the image segmentation based on a segmentation technique.

In some embodiments, assuming that a configuration of the actual grafted vessel remains (substantially) the same before and after the interventional therapy, the processing device 140 may determine the first model based on the second model of the object. The processing device 140 may determine the first model of the object by removing the configuration of the actual grafted vessel from the second model of the object. In some embodiments, the processing device 140 may determine the first model of the object by further performing a filling operation on the remaining portion of the second model of the object. For example, the filling operation may include utilizing a predetermined pixel value or voxel value to fill the remaining portion of the second model of the object.

In some embodiments, the processing device 140 may determine the configuration of the actual grafted vessel by performing, based on the second model of the object, a segmentation with respect to the actual grafted vessel. The segmentation used herein may refer to a segmentation of a representation of the actual grafted vessel from the second model of the training object. The processing device 140 may perform the segmentation based on a segmentation technique. For example, the segmentation technique may include a region-based segmentation technique, an edge-based segmentation technique, a wavelet transform segmentation technique, a mathematical morphology segmentation technique, a genetic algorithm-based segmentation technique, or the like, or a combination thereof. In some embodiments, the processing device 140 may determine the configuration of the actual grafted vessel by removing the first model from the second model.

In some embodiments, the processing device 140 may determine the configuration of the actual grafted vessel based on the second model using a second vessel determination model. The second vessel determination model may be the same as or different from the vessel determination model configured to determine the configuration of the vessel. In some embodiments, the process for determining the second vessel determination model may be the same as or similar to the process for determining the vessel determination model.

In some embodiments, the quantification result may include a second quantification result determined based on the preoperative blood parameter and an actual postoperative blood parameter. In some embodiments, the processing device 140 may determine the actual postoperative blood parameter based on the actual postoperative model and the specific data of the object. The second quantification result may be used to evaluate the efficacy of an actual interventional therapy including grafting the actual vessel to the object, facilitating an operator (e.g., a doctor) in clinical decision-making and/or planning a subsequent therapy for the object in a non-invasive manner. More descriptions of the utilization of the second qualification result may be found elsewhere in the present disclosure. See, for example, FIG. 7 and/or the descriptions thereof.

In some embodiments, the quantification result may include a difference between the virtual postoperative blood parameter and the actual postoperative blood parameter. The difference may be expressed as an absolute value, a percentage, a ratio, etc. If the difference between the virtual postoperative blood parameter and the actual postoperative blood parameter is larger than or equal to a difference threshold, the processing device 140 may determine that a probability of a clinical event of the object after the actual interventional therapy may be larger than or equal to a probability threshold (e.g., 50%, 75%). A subsequent therapy for the object may need to be planned according to the probability of the clinical event of the object. Besides, if the difference between the virtual postoperative blood parameter and the actual postoperative blood parameter is larger than or equal to a difference threshold, an assessment or determination may be made as to whether there is a clinical problem of the actual intervention therapy, thereby optimizing the planning and/or execution of a subsequent interventional therapy on the same object or a different object.

FIG. 6 is a flowchart illustrating an exemplary process for blood parameter assessment according to some embodiments of the present disclosure. In some embodiments, process 600 may be executed by the blood parameter assessment system 100. For example, the process 600 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 600. The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 140 (e.g., the result determination module 440) may determine whether a quantification result satisfies a predetermined condition. The quantification result used herein may include the first quantification result determined based on the preoperative blood parameter and the virtual postoperative blood parameter as illustrated in FIG. 5.

In some embodiments, the predetermined condition may include that the first quantification result is within a predetermined range. In some embodiments, the predetermined condition may include that the virtual postoperative blood parameter may be within the predetermined range (e.g., a clinical reference range). In some embodiments, the predetermined condition may include that a blood flow, a blood pressure, a wall shear stress, an FFR value at each of one or more points, locations, or regions of the virtual postoperative blood parameter may be within a predetermined range, respectively. For example, the predetermined range of the wall shear stress of the virtual postoperative blood parameter may be a range exceeding 1.5 Pa. In some embodiments, the predetermined condition may include a probability of the occurrence of a clinical event of the object after the virtual interventional therapy is smaller than a probability threshold (e.g., 50%, 75%). For example, the clinical event of the object may include stenosis of a virtual grafted vessel, spasm of the virtual grafted vessel, recurrent myocardial ischemia, myocardial infarction, vessel revascularization, etc.

In response to determining that the quantification result satisfies the predetermined condition, the processing device 140 may determine that the virtual grafted vessel is acceptable and plan an actual interventional therapy of the object according to the feature information of the virtual grafted vessel. In some embodiments, the processing device 140 may determine feature information of the virtual grafted vessel as feature information of an actual grafted vessel for an actual interventional therapy of the object.

In 620, in response to determining that the quantification result fails to satisfy the predetermined condition, the processing device 140 (e.g., the result determination module 440) may determine that the feature information of the virtual grafted vessel needs to be adjusted.

Figure 8:
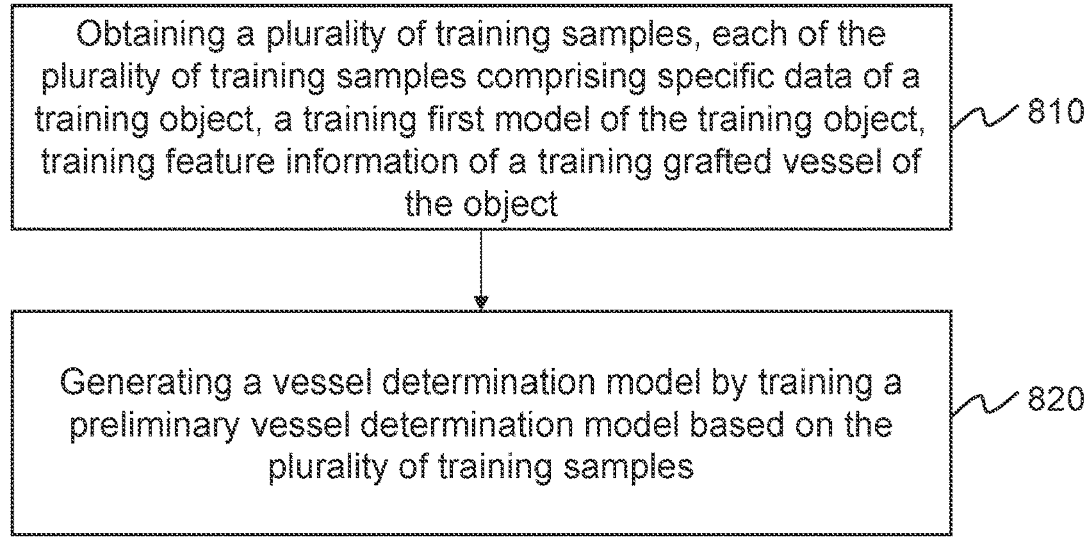
FIG. 8 is a flowchart illustrating an exemplary process for generating a vessel determination model according to some embodiments of the present disclosure.

In 630, the processing device 140 (e.g., the result determination module 440) may determine, using a vessel determination model (e.g., the vessel determination model as illustrated in FIG. 5 or FIG. 8), an adjusted configuration of an adjusted virtual grafted vessel based on specific data of the object (e.g., the specific data of the object as illustrated in FIG. 5) and the adjusted feature information of the adjusted virtual grafted vessel. The process for determining the adjusted configuration of the adjusted virtual grafted vessel may be the same as or similar to the process for determining the configuration of the virtual grafted vessel in FIG. 5, the descriptions of which are not repeated.

In 640, the processing device 140 (e.g., the result determination module 440) may determine an adjusted second model by combining the adjusted configuration of the adjusted virtual grafted vessel and the first model of the object. The process for determining the adjusted second model may be the same as or similar to the process for determining the second model in FIG. 5, the descriptions of which are not repeated.

In 650, the processing device 140 (e.g., the result determination module 440) may determine an adjusted second blood parameter based on the adjusted second model and the specific data of the object. The process for determining the adjusted second blood parameter may be the same as or similar to the process for determining the adjusted second blood parameter in operation 550, the descriptions of which are not repeated.

In 660, the processing device 140 (e.g., the result determination module 440) may determine an adjusted quantification result of the object based on a first blood parameter (e.g., the first blood parameter determined as illustrated in FIG. 5) and the adjusted second blood parameter. The process for determining the adjusted quantification result of the object may be the same as or similar to the process for determining the quantification result of the object in operation 560, the descriptions of which are not repeated.

In some embodiments, the processing device 140 may repeat the process 600 until a current adjusted quantification result of the object satisfies the predetermined condition. The processing device 140 may plan an actual interventional therapy of the object according to current feature information of the virtual grafted vessel corresponding to the current adjusted quantification result. In some embodiments, the processing device 140 may determine the current feature information of the virtual grafted vessel corresponding to the current adjusted quantification result as feature information of an actual grafted vessel for the actual interventional therapy.

According to the process 600, the actual interventional therapy of the object may be planned based on a virtual interventional therapy that has a relatively better effect among various virtual interventional therapies, thereby positively improving an effect of the actual therapy of the object.

FIG. 7 is a flowchart illustrating an exemplary process for blood parameter assessment according to some embodiments of the present disclosure. In some embodiments, process 700 may be executed by the blood parameter assessment system 100. For example, the process 700 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 700. The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 140 (e.g., the result determination module 440) may determine whether a quantification result satisfies a predetermined condition. The quantification result used herein may include the second quantification result determined based on the preoperative blood parameter and the actual postoperative blood parameter as illustrated in operation 560.

In some embodiments, the predetermined condition may include that the second quantification result is within a predetermined range. In some embodiments, the predetermined condition may include that the actual postoperative blood parameter may be within the predetermined range (e.g., a clinical reference range). In some embodiments, the predetermined condition may include that a blood flow, a blood pressure, a wall shear stress, an FFR value at one or more points, locations, or regions of the actual postoperative blood parameter may be within a predetermined range, respectively. For example, the predetermined range of the wall shear stress of the actual postoperative blood parameter may be a range exceeding 1.5 Pa.

In 720, the processing device 140 (e.g., the result determination module 440) may determine a probability of a clinical event of the object based on whether the quantification result satisfies a predetermined condition. In some embodiments, the clinical event of the object may include stenosis of an actual grafted vessel, spasm of an actual grafted vessel, recurrent myocardial ischemia, myocardial infarction, vessel revascularization, etc.

In some embodiments, in response to determining that the quantification result satisfies the predetermined condition, the processing device 140 may determine that the probability of the clinical event of the object is smaller than a probability threshold (e.g., 50%, 75%), which means that the effect of the actual interventional therapy may be acceptable or satisfactory. In such cases, the object may need to be monitored regularly. In response to determining that the quantification result fails to satisfy the predetermined condition, the processing device 140 may determine that the probability of the clinical event of the object is larger than or equal to the probability threshold, which means that the efficacy of the actual interventional therapy or a postoperative recovery may be unacceptable or unsatisfactory. In such cases, the object may need to be monitored closely (more than regular monitoring), and/or a subsequent therapy of the object may need to be planned and/or executed.

FIG. 8 is a flowchart illustrating an exemplary process for generating a vessel determination model according to some embodiments of the present disclosure. In some embodiments, process 800 may be executed by the blood parameter assessment system 100. For example, the process 800 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or a module in the processing device 140B illustrated in FIG. 4B) may execute the set of instructions and may accordingly be directed to perform the process 800. The operations of the illustrated process 800 presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, the vessel determination model and/or the second vessel determination model as illustrated in FIG. 5 may be trained based on the process 800.

In 810, the processing device 140B (e.g., the vessel model generation module 470) may obtain a plurality of training samples. Each of the plurality of training samples may include training specific data of a training object, a training first model of the training object, and/or training feature information of a training grafted vessel of the object. In some embodiments, the training object had a heart disease (e.g., a coronary artery disease (CAD)) and a training interventional therapy (e.g., a bypass surgery) was performed on the training object.

In some embodiments, similar to the specific data of the object already described in connection with FIGS. 5-7, the training specific data of the training object may include a systolic pressure, a diastolic pressure, a heart rate, a cardiac output, a blood property (e.g., an amount, a blood volume, a viscosity, a specific gravity, pH, a temperature, an osmotic pressure, a color, a blood type), a gender, an age, a height, a weight, a medical history, smoking, diabetes, hypertension, imaging data of the training object, or the like, or any combination thereof.

In some embodiments, similar to the first model of the object already described in connection with FIGS. 5-7, the training first model of the training object may include training cardiac anatomy information of at least a portion of a heart of the training object. In some embodiments, the training first model of the object may include training cardiac anatomy information of the whole heart of the training object. In some embodiments, the training first model of the object may include training cardiac anatomy information of only a portion of the heart of the training object.

In some embodiments, the training cardiac anatomy information of the at least a portion of the heart of the training object may include a configuration (e.g., a 3D configuration, a 2D configuration) of the at least a portion of the heart, etc. In some embodiments, the training first model (also referred to as a training preoperative model) may include the training cardiac anatomy information of the training object before the training interventional therapy was performed on the object. Accordingly, the training first model may include a configuration (e.g., a 3D configuration, a 2D configuration) of the at least a portion of the heart, etc., before the training interventional therapy was performed on the training object.

In some embodiments, similar to the feature information of the grafted vessel of the object already described in connection with FIGS. 5-7, the training feature information of the training grafted vessel may be determined based on a planned training interventional therapy, instead of an actual training interventional therapy that was performed on the training object. In some embodiments, the training feature information of the training grafted vessel may include one or more anastomosis positions between the training grafted vessel and a coronary artery, a length of the training grafted vessel, a diameter of the training grafted vessel at one or more points or locations, a length of the training grafted vessel between the one or more anastomosis positions, an angle between the training grafted vessel and an aorta at one of the one or more anastomosis positions, or an angle between the training grafted vessel and a coronary artery at one of the one or more anastomosis positions. More descriptions of the training specific data, the training first model, and/or the training feature information of the training grafted vessel may be found elsewhere in the present disclosure, for example, FIG. 5 or the descriptions thereof.

In some embodiments, the processing device 140B may obtain the training samples from a storage device (e.g., the storage device 150, the storage 220, the storage 390) disclosed elsewhere in the present disclosure or a third party (e.g., an external device) (e.g., a pathological information database, a scanning image database).

In 820, the processing device 140 (e.g., the vessel model generation module 470) may generate the vessel determination model by training a preliminary vessel determination model based on the plurality of training samples. In some embodiments, the preliminary vessel determination model may include a machine learning model (e.g., a neural network model). For example, the preliminary vessel determination model may include a convolutional neural network (CNN) model, a recurrent neural network (RNN) model, a long short term memory (LSTM) network model, a fully convolutional neural network (FCN) model, a generative adversarial network (GAN) model, a Hopfield model, a dilated convolution model, a conditional random fields as recurrent neural networks (CRFasRNN) model, or the like, or any combination thereof.

In some embodiments, the preliminary vessel determination model may include a plurality of parameters (also referred to as "training parameters"). For example, the training parameters may include the size of a kernel of a layer, the total count (or number) of layers, the count (or number) of nodes in a layer, a learning rate, a batch size, an epoch, a connected weight between two connected nodes, a bias vector relating to a node, an activation vector of a node in a layer, or the like, or any combination thereof. In some embodiments, the processing device 140B may initialize or set the training parameters.

In some embodiments, for each of at least part of the plurality of training samples (also referred to as first training samples), the processing device 140B may generate a training configuration of the training vessel using the first training sample and the preliminary vessel determination model or an intermediate vessel determination model determined based on the preliminary vessel determination model during the training process as described elsewhere in the present disclosure. In some embodiments, the processing device 140B may input the first training sample into the preliminary or intermediate vessel determination model and the training configuration of the training vessel may be output by the preliminary or intermediate vessel determination model.

In some embodiments, the processing device 140B may obtain a comparison result by comparing the training configuration of the training vessel and a reference configuration of the training vessel corresponding to the first training sample. The reference configuration of the training vessel may be a desired output of the preliminary or intermediate vessel determination model corresponding to the first training sample. The reference configuration of the training vessel may also be referred to as a mask or ground truth corresponding to the first training sample. In some embodiments, the processing device 140 may obtain a training second model of the training object. The processing device 140 may determine the reference configuration of the training grafted vessel by performing, based on the training second model of the training object, a segmentation with respect to the training grafted vessel. The segmentation used herein may refer to a segmentation of a representation of the training grafted vessel from the training second model of the training object. The processing device 140 may perform the segmentation based on a segmentation technique. For example, the segmentation technique may include a region-based segmentation technique, an edge-based segmentation technique, a wavelet transform segmentation technique, a mathematical morphology segmentation technique, a genetic algorithm-based segmentation technique, or the like, or a combination thereof.

It should be noted that the above descriptions are non-limiting. In some embodiments, the processing device 140 may further determine reference feature information of a training grafted vessel based on the reference configuration of the training grafted vessel. The reference feature information of the training grafted vessel may be used as a desired output of a training sample during the training of the vessel determination model. The vessel determination model so trained may also be used to determine feature information of a grafted vessel (e.g., an actual grafted vessel, a virtual grafted vessel).

In some embodiments, the comparison result may be used to assess a difference between the training configuration of the training grafted vessel and the reference configuration of the training grafted vessel. In some embodiments, the processing device 140B may determine an objective function based on the difference as the comparison result. For example, the objective function may include a loss function of the difference, a root mean square error (RMSE) function, a mean absolute error (MAE) function, etc.

In some embodiments, the processing device 140B may generate the vessel determination model by performing a plurality of iterations to iteratively update one or more training parameters of the preliminary vessel determination model. For example, the processing device 140B may update the training parameters based on the objective function using a backpropagation (BP) algorithm. A preliminary vessel determination model with one or more updated training parameters in one iteration of the plurality of iterations may be referred to as an updated or intermediate vessel determination model. In each iteration, the processing device 140B may generate a training configuration of the training grafted vessel corresponding to one first training sample using the preliminary vessel determination model or the updated preliminary vessel determination model.

In some embodiments, the processing device 140B may determine whether to terminate the training process by determining whether a predetermined condition (or referred to a termination condition) is satisfied. In response to determining that the predetermined condition is satisfied, the processing device 140B may designate the preliminary or updated vessel determination model as the vessel determination model. On the other hand, in response to determining that the predetermined condition is not satisfied, the processing device 140B may further update the preliminary or updated vessel determination model. In some embodiments, the processing device 140B may update the preliminary or updated vessel determination model using at least a part of the first training samples.

In some embodiments, the predetermined condition may relate to the comparison result between the training configuration of the training grafted vessel and the reference configuration of the training grafted vessel. In some embodiments, the predetermined condition may be satisfied if the value of the objective function is (locally or globally) minimal or smaller than a threshold (e.g., a constant). In some embodiments, the predetermined condition may be satisfied if the value of the objective function converges. The convergence may be deemed to have occurred if the variation of the values of the objective function in two or more consecutive iterations is smaller than a threshold (e.g., a constant).

In some embodiments, the predetermined condition may include, additionally or alternatively, whether a specified count (or number) of iterations (or rounds of training) have been performed, whether parameters of the preliminary or updated vessel determination model converge within a certain rounds/iterations (e.g., three rounds/iterations, five rounds/iterations) of training, etc. For instance, the predetermined condition may be deemed satisfied when the objective function based on the comparison result is (locally or globally) minimal or smaller than a threshold (e.g., a constant) and at least a certain count or number of iterations (or rounds of training) have been performed. As another example, the predetermined condition may be deemed satisfied either when the objective function based on the comparison result converges or when parameters of the preliminary or updated vessel determination model and parameters of the preliminary or updated vessel determination model converge within a certain rounds (e.g., three rounds, five rounds) of training. In some embodiments, the processing device 140B may transmit the vessel determination model, to a storage device (e.g., the storage device 150, the storage 220, and the storage 390) for storage.

In some embodiments, the processing device 140B may use at least a part of the training samples (also referred to as second training samples) to validate the vessel determination model. In some embodiments, the second training samples may be different from the first training samples as illustrated below. In some embodiments, the processing device 140B may process the second training samples using the vessel determination model to generate a validating configuration of a training grafted vessel in each of the second training samples. The processing device 1406 may obtain a validating comparison result by comparing the validating configuration of the training grafted vessel with a reference configuration of the training grafted vessel. If the validating comparison result fails to satisfy a predetermined validating condition, the processing device 140B may retrain the vessel determination model until a new validating comparison result satisfies the predetermined condition, and a model so obtained may be the vessel determination model as illustrated in FIG. 5. For example, the processing device 140B may use at least a part of the training samples (also referred to as "third training samples") to retrain the vessel determination model. In some embodiments, the third training samples may be the same as or different from the first training samples and/or the second training samples. In some embodiments, the process for retraining the vessel determination model using the third training samples may be the same as training the preliminary vessel determination model using the first training samples as illustrated above. As used herein, the predetermined validating condition may include a difference between the validating result(s) and the reference validating result(s) being smaller than a preset validating threshold.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:

at least one storage device including a set of instructions;

at least one processor in communication with the at least one storage device, wherein when executing the set of instructions, the at least one processor is configured to cause the system to perform operations including:

acquiring specific data of an object;

determining a first model of the object, the first model comprising cardiac anatomy information of at least a portion of a heart of the object;

determining a first blood parameter of the object based on the specific data of the object and the first model of the object;

determining a second model of the object, the second model comprising a configuration of a grafted vessel of the object, the grafted vessel comprising a virtual grafted vessel;

determining a second blood parameter of the object based on the specific data of the object and the second model of the object;

determining a quantification result of the object based on the first blood parameter and the second blood parameter by:

determining whether the quantification result satisfies a predetermined condition;

in response to determining that the quantification result fails to satisfy the predetermined condition, adjusting feature information of the virtual grafted vessel;

determining, using a vessel determination model, an adjusted configuration of an adjusted virtual grafted vessel based on the specific data of the object and the adjusted feature information;

determining an adjusted second model by combining the adjusted configuration of the adjusted virtual grafted vessel and the first model of the object;

determining an adjusted second blood parameter based on the adjusted second model and the specific data of the object; and determining an adjusted quantification result of the object based on the first blood parameter and the adjusted second blood parameter; and planning actual interventional therapy of the object according to the adjusted feature information of the virtual grafted vessel corresponding to the adjusted quantification result.

2. The system of claim 1, wherein the specific data of the object includes at least one of a systolic pressure, a diastolic pressure, a heart rate, a cardiac output, a blood property, a gender, an age, a height, a weight, a medical history, smoking, diabetes, hypertension, or imaging data of the object.

3. The system of claim 1, wherein the first blood parameter of the object includes at least one of a blood pressure, a blood flow velocity, a blood flow flux, or a wall shear stress at each of one or more points or each of one or more regions of the first model of the object or one or more computed results determined based on at least one of the blood pressure, the blood flow velocity, the blood flow flux, or the wall shear stress.

4. The system of claim 1, wherein the second blood parameter of the object includes at least one of a blood pressure, a blood flow velocity, a blood flow flux, or a wall shear stress at each of one or more points or each of one or more regions of the second model of the object or one or more computed results determined based on at least one of the blood pressure, the blood flow velocity, the blood flow flux, or the wall shear stress.

5. The system of claim 1, wherein the determining the first model of the object includes:

obtaining imaging data of the object acquired by scanning the object; and determining the first model of the object by performing, based on the imaging data, an image segmentation with respect to the at least a portion of the heart.

6. The system of claim 1, wherein the determining the second model of the object includes:

determining a configuration of the virtual grafted vessel of the object based on the vessel determination model; and determining the second model of the object by combining the first model and the configuration of the virtual grafted vessel.

7. The system of claim 6, wherein the determining the configuration of the virtual grafted vessel of the object based on the vessel determination model includes:

obtaining the feature information of the virtual grafted vessel of the object; and determining the configuration of the virtual grafted vessel by inputting the specific data of the object, the feature information of the virtual grafted vessel, and the first model into the vessel determination model.

8. The system of claim 7, wherein the feature information of the virtual grafted vessel includes at least one of one or more anastomosis positions between the virtual grafted vessel and a coronary artery, a length of the virtual grafted vessel, a diameter of the virtual grafted vessel at one or more points, a length of the virtual grafted vessel between the one or more anastomosis positions, an angle between the virtual grafted vessel and an aorta at one of the one or more anastomosis positions, or an angle between the virtual grafted vessel and a coronary artery at one of the one or more anastomosis positions.

9. The system of claim 6, wherein the vessel determination model is determined by a training process including:

obtaining a plurality of training samples, each of the plurality of training samples comprising training specific data of a training object, a training first model of the training object, training feature information of a training grafted vessel of the object; and generating the vessel determination model by training a preliminary vessel determination model based on the plurality of training samples.

10. The system of claim 1, the grafted vessel comprising an actual grafted vessel, wherein the determining the second model of the object includes:

obtaining imaging data of the object acquired by scanning the object; and determining the second model of the object by performing, based on the imaging data, an image segmentation with respect to the at least a portion of the heart and the actual grafted vessel.

11. The system of claim 1, the grafted vessel comprising an actual grafted vessel, wherein the determining the first model of the object includes:

determining a configuration of the actual grafted vessel based on the second model of the object; and determining the first model of the object by removing the configuration of the actual grafted vessel from the second model.

12. The system of claim 11, wherein the determining the configuration of the actual grafted vessel based on the second model of the object includes:

determining the configuration of the actual grafted vessel based on the feature information of the actual grafted vessel and the second model of the object using a second vessel determination model.

13. The system of claim 1, wherein the determining the first blood parameter of the object based on the specific data of the object and the first model of the object includes:

meshing the first model of the object; and determining the first blood parameter of the object based on the specific data of the object and the meshed first model.

14. The system of claim 1, wherein the determining the second blood parameter of the object based on the specific data of the object and the second model of the object includes:

meshing the second model of the object; and determining the second blood parameter of the object based on the specific data of the object and the meshed second model.

15. The system of claim 1, wherein the determining the quantification result of the object based on the first blood parameter and the second blood parameter includes:

determining a difference between the first blood parameter and the second blood parameter; and determining the quantification result of the object based on the difference.

16. The system of claim 1, wherein the determining the quantification result of the object based on the first blood parameter and the second blood parameter includes:

determining a ratio between the first blood parameter and the second blood parameter; and determining the quantification result of the object based on the ratio.

17. The system of claim 1, the grafted vessel comprising an actual grafted vessel, wherein the determining the quantification result of the object based on the first blood parameter and the second blood parameter includes:

determining whether the quantification result satisfies a predetermined condition; and determining a probability of a clinical event of the object based on whether the quantification result satisfies a predetermined condition.

18. A method implemented on a computing device having at least one processor, and at least one storage device, the method comprising:

acquiring specific data of an object;

determining a first model of the object, the first model comprising cardiac anatomy information of at least a portion of a heart of the object;

determining a first blood parameter of the object based on the specific data of the object and the first model of the object;

determining a second model of the object, the second model comprising a configuration of a grafted vessel of the object, the grafted vessel comprising a virtual grafted vessel;

determining a second blood parameter of the object based on the specific data of the object and the second model of the object;

determining a quantification result of the object based on the first blood parameter and the second blood parameter by:

determining whether the quantification result satisfies a predetermined condition;

in response to determining that the quantification result fails to satisfy the predetermined condition, adjusting feature information of the virtual grafted vessel;

determining, using a vessel determination model, an adjusted configuration of an adjusted virtual grafted vessel based on the specific data of the object and the adjusted feature information;

determining an adjusted second model by combining the adjusted configuration of the adjusted virtual grafted vessel and the first model of the object;

determining an adjusted second blood parameter based on the adjusted second model and the specific data of the object; and determining an adjusted quantification result of the object based on the first blood parameter and the adjusted second blood parameter; and planning actual interventional therapy of the object according to the adjusted feature information of the virtual grafted vessel corresponding to the adjusted quantification result.

19. A non-transitory computer readable medium, comprising at least one set of instructions, wherein when executed by at least one processor of a computing device, the at least one set of instructions cause the at least one processor to effectuate a method comprising:

acquiring specific data of an object;

determining a first model of the object, the first model comprising cardiac anatomy information of at least a portion of a heart of the object;

determining a first blood parameter of the object based on the specific data of the object and the first model of the object;

determining a second model of the object, the second model comprising a configuration of a grafted vessel of the object, the grafted vessel comprising a virtual grafted vessel;

determining a second blood parameter of the object based on the specific data of the object and the second model of the object; and determining a quantification result of the object based on the first blood parameter and the second blood parameter by:

determining whether the quantification result satisfies a predetermined condition;

in response to determining that the quantification result fails to satisfy the predetermined condition, adjusting feature information of the virtual grafted vessel;

determining, using a vessel determination model, an adjusted configuration of an adjusted virtual grafted vessel based on the specific data of the object and the adjusted feature information;

determining an adjusted second model by combining the adjusted configuration of the adjusted virtual grafted vessel and the first model of the object;

determining an adjusted second blood parameter based on the adjusted second model and the specific data of the object; and determining an adjusted quantification result of the object based on the first blood parameter and the adjusted second blood parameter; and planning actual interventional therapy of the object according to the adjusted feature information of the virtual grafted vessel corresponding to the adjusted quantification result.

* * * * *